(12) United States Patent
Boches et al.

(10) Patent No.: US 6,555,388 B1
(45) Date of Patent: Apr. 29, 2003

(54) BINDING PROTEIN CAPTURE ASSAY

(75) Inventors: Francee Boches, Miami, FL (US); Kathy F. Hilyard, Pembroke Pine, FL (US); James Monticello, Miami, FL (US); Dennis Smith, Cooper City, FL (US); Richard Timmons, Miami, FL (US)

(73) Assignee: Dade Behring Inc., Deerfield, IL (US)

( * ) Notice: Subject to any disclaimer, the term of this patent is extended or adjusted under 35 U.S.C. 154(b) by 0 days.

(21) Appl. No.: 08/150,747

(22) Filed: Nov. 12, 1993

Related U.S. Application Data

(63) Continuation of application No. 08/029,932, filed on Mar. 9, 1993, which is a continuation of application No. 07/817,139, filed on Jan. 6, 1992.

(51) Int. Cl.$^7$ ............................................. G01N 33/543
(52) U.S. Cl. ...................... 436/501; 436/505; 436/518; 436/524; 436/527; 436/533; 436/536; 436/538; 436/540; 436/7.1; 436/7.92; 436/7.93; 436/7.94; 436/7.95
(58) Field of Search ................................ 436/501, 505, 436/518, 524, 527, 533, 536, 538, 540; 435/792, 793, 794, 795

(56) References Cited

U.S. PATENT DOCUMENTS

| | | | | |
|---|---|---|---|---|
| 4,028,465 A | * | 6/1977 | Lewin et al. | 424/1 |
| 4,092,408 A | * | 5/1978 | Litt | 424/1 |
| 4,146,602 A | * | 3/1979 | Gutcho et al. | 424/1 |
| 4,300,907 A | * | 11/1981 | Mansbach et al. | 23/230 B |
| 4,332,786 A | * | 6/1982 | Cabelli et al. | 424/1 |
| 4,418,151 A | * | 11/1983 | Forand et al. | 436/505 |
| 4,423,154 A | * | 12/1983 | Gutcho et al. | 436/505 |
| 4,426,455 A | * | 1/1984 | Tovey et al. | 436/505 |
| 4,451,571 A | * | 5/1984 | Allen | 436/505 |
| 4,806,493 A | * | 2/1989 | Yuan | 436/505 |
| 4,943,522 A | * | 7/1990 | Eisinger et al. | 435/7 |
| 4,950,612 A | * | 8/1990 | Khanna et al. | 436/505 |

FOREIGN PATENT DOCUMENTS

| | | | |
|---|---|---|---|
| WO | WO 91 00519 | | 6/1990 |
| WO | 9100519 | * | 1/1991 |

OTHER PUBLICATIONS

Hoier–Madsen, M. et al, "Rabbit Antibodies Against the Low Molecular Weight Folate Binding Protein from Human Milk. Use for Immunological Characterization of Human Folate Binding Proteins in an Enzyme–Linked Immunosorbent Assay (ELISA)", Bioscience Reports, vol. 7, No. 7, pp. 553–557, 1987.*
Suter, M. et al, "The Immunochemistry of Sandwich ELISAs. II. A Novel System Prevents the Denaturation of Capture Antibodies", Immunology Letters, vol. 13, pp. 313–316, 1986.*
Jacob et al (1972) J Clin Path 25:320–325.*
Van de Wiel et al (1974) Clin Chim Acta 56:143–149.*
Endres et al (1978) Clin Chem 24(3):460–465.*
White et al (1986) Medical Virology Academic Press, NY pp 330–334.*
BIO–RAD Quantaphase$^R$ B–12/Folate Radioassay, B–12 Radioassay and Folate Radioassay; Instruction Manual. Date of Publication: Apr. 1989.

* cited by examiner

*Primary Examiner*—Bao-Thuy L. Nguyen
(74) *Attorney, Agent, or Firm*—Cynthia G. Tymeson; Louise S. Pearson

(57) ABSTRACT

This invention relates to binding protein assays. In particular, this invention relates to binding protein assays for B12 and folate in serum or plasma. More specifically, this invention provides a sequential assay that uses a combination of specific binding proteins, and anti-binding protein antibodies to measure B12 and folate in serum or plasma.

3 Claims, 2 Drawing Sheets

BINDING PROTEIN CAPTURE ASSAY

This is a continuation of application Ser. No. 08/029,932, filed on Mar. 9, 1993, which is a continuation of U.S. Ser. No. 07/817,139, filed on Jan. 6, 1992.

BACKGROUND OF THE INVENTION

1. Field of the Invention

This invention is directed to binding protein assays. More particularly, this invention concerns itself with binding protein assays for B12 and folate in serum or plasma.

2. Descriptions of the Prior Art

Certain analytes are found in circulation in multiple physiologically active metabolic states. Antibodies raised to an analyte in a physiologically active class of analytes generally only bind to one metabolite and are not useful in detecting total metabolite concentration. To solve this problem, specific binding proteins have been used to bind an entire class of physiologically active metabolites. For example B12 and folate are assayed using either the intrinsic factor or folate binding protein respectively adsorbed directly on to latex particles. The unknown analyte then competes with a radioactively labeled analyte or analyte analogue for these bound binding proteins. See e.g. OUAN-TAPHASE (Bio-Rad). These assays, however, are labor intensive. Thus, a continuing need exists to develop a simplified method to measure total concentration of physiologically active analyte classes.

One recent approach to this problem is disclosed in European patent application WO 91/00519. This application discloses an immunoassay for vitamin B12 using monoclonal antibodies to intrinsic factor: vitamin B12 complex and to the vitamin B12 binding site on intrinsic factor. In a competitive assay, vitamin B12 competes with labelled monoclonal antibodies for binding to intrinsic factor. It is reported that the use of these site-specific antibodies in such as assay enables indirect measurement of vitamin B12, as the vitamin B12 levels are measured by monitoring antibodies binding to intrinsic factor. Still other techniques, however, are needed to measure total concentration of physiologically active analyte classes.

SUMMARY OF THE INVENTION

Accordingly, it is an object of this invention to remedy the above discussed deficiencies. In particular, this invention provides competitive binding protein capture assays that use a combination of specific binding proteins and anti-binding protein antibodies. More specifically, this invention provides: a method for conducting a solid phase binding protein capture assay of a fluid sample with primary antibody that binds to the binding protein, the fluid sample containing an unknown amount of analyte that binds with binding proteins, the method involving: treating the fluid sample to free the analyte from endogenous binding proteins; combining under binding conditions free analyte, the primary antibody and the binding protein to form a mixture of analyte-binding protein-primary antibody and binding protein-primary antibody complexes; applying the fluid mixture under binding conditions to a solid support selectively retentive of the complexes; applying an indicator to the solid support under binding conditions wherein the indicator binds to unoccupied binding sites of the binding protein-primary antibody complex bound to the solid support; observing the extent to which the indicator is present on the solid support; correlating the extent to which the indicator is present with the amount of unknown analyte in the sample. Binding conditions are further delineated in P. Tijssen, *Laboratory Techniques in Biochemistry*, Molecular Biology, Practice and Theory of Enzyme Immunoassay 123–145. (4th ed. 1987) (hereby incorporated by reference). Additionally, the terminology indicator in the context of this invention means a labeled conjugate. The conjugate is an analyte. The label is a fluorescent, enzymatic, colorometric or radiometric compound that is associated either directly or indirectly with the conjugate. The label may be comprised of an enzymatic compound that produces fluorescence upon contact with a substrate. The extent to which the indicator is present on the solid support can be correlated with the amount of unknown analyte. P. Tijssen, *Laboratory Techniques in Biochemistry*, Molecular Biology, Practice and Theory of Enzyme Immunoassay 173–217 and 368–37E). (4th ed. 1987) (hereby incorporated by reference).

This invention further provides a method for conducting a solid phase binding protein capture assay of a fluid sample with primary antibody that bind to binding protein, the fluid sample containing an unknown amount of analyte that binds binding proteins, the method involving: immobilizing a sufficient amount of a first agent selectively retentive of primary antibody or modified primary antibody and a primary antibody; treating the fluid sample to free the analyte from endogenous binding protein; combining under binding conditions free analyte and the binding protein to form a mixture of analyte-binding protein complex and free binding protein; applying the fluid mixture under binding conditions to a the solid support selectively retentive of the complexes and free binding protein; applying an indicator to the solid support under binding conditions to bind with unoccupied binding sites of the binding protein bound to the solid support; observing the extent to which the indicator is present on the solid phase; correlating the extent to which the bound indicator is present with the amount of unknown analyte in the sample.

This invention further provides a method for conducting a solid phase binding protein capture assay of a fluid sample with primary antibody to binding protein, the fluid sample containing an unknown amount of analyte that binds binding protein, the method involving: immobilizing a sufficient amount of antibody to specific animal species to bind antibodies from that species or a homologous species on a solid support; treating the fluid mixture to free analyte from endogenous binding proteins, combining under binding conditions: free analyte, the binding protein, and primary antibody of the specific animal species to form a mixture of analyte-binding protein-primary antibody and binding protein-primary antibody complexes; applying the fluid mixture under binding conditions to the solid support; applying an indicator to the solid support under binding conditions to bind with unoccupied binding sites of the binding protein-antibody complex bound to the solid support; observing the extent to which the indicator is present on the solid phase; correlating the extent to which the indicator is present with the amount of unknown analyte in the sample.

This invention further provides: a method for conducting a solid phase binding protein capture assay of a fluid sample with primary antibody to binding protein, within the interstices of a solid, inert porous medium, the fluid sample containing an unknown amount of analyte that binds binding protein, the method involving: immobilizing a sufficient amount of antibody to specific animal species to bind antibodies from that species or a homologous species within a finite zone of the interstices of the matrix; treating the fluid sample to free analyte from endogenous binding proteins;

combining under binding conditions: free analyte, primary antibody of the specific animal species and the binding protein to form a mixture of analyte-binding protein-primary antibody and binding protein-primary antibody complexes; applying the fluid mixture under binding conditions to center of the finite zone to bind the complexes to the immobilized antibody to a specific species; applying an indicator to the solid support under binding conditions to bind with unoccupied binding sites of the binding protein-antibody complex bound to the solid support; observing the extent to which the indicator is present within a delimited area of the reaction zone; and correlating the extent to which the bound indicator is present in the delimited area with the amount of unknown analyte in the sample.

This invention further provides: a method for conducting a solid phase binding protein capture assay of a fluid sample with primary antibody to binding protein, the fluid sample containing an unknown amount of analyte that binds binding protein, the method involving: immobilizing a sufficient amount of binding protein with a primary antibody bound to a solid support; treating the fluid sample to free analyte from endogenous binding proteins; applying free analyte under binding conditions to the solid support; applying an indicator to the solid support under binding conditions to bind with unoccupied binding sites of the binding protein-antibody complex bound to the solid support; observing the extent to which the indicator is present; correlating the extent to which the indicator is present with the amount of unknown analyte in the sample.

This invention further provides: a method for conducting a solid phase binding protein capture assay of a fluid sample with primary antibody to binding protein within the interstices of a solid, inert porous medium, the fluid sample containing an unknown amount of analyte that binds binding protein, the method involving: immobilizing a fixed amount of binding protein with an antibody to the binding protein, the antibody being of a specific or homologous species, the antibody being bound by an antibody against that species or a homologous species immobilized within a finite zone of the interstices of the medium; treating the fluid mixture to free analyte from endogenous binding proteins; applying the analyte under binding conditions to the center of the finite zone to bind the binding proteins; applying an indicator to the solid support under binding conditions to bind with unoccupied binding proteins; observing the extent to which the indicator is present within a delimited area of the reaction zone; and correlating the extent to which the indicator is present: in the delimited area with the amount of unknown analyte in the sample.

This invention further provides: a method for conducting a solid phase binding protein capture assay a fluid sample with primary antibody to binding protein, the fluid sample containing an unknown amount of analyte that binds binding protein, the method involving: immobilizing a sufficient amount of primary antibody on to a solid support; treating the fluid mixture to free analyte from endogenous binding proteins; combining under binding conditions binding protein and free analyte to form a fluid mixture; applying the fluid mixture under binding conditions to the solid support; applying an indicator to the solid support under binding conditions to bind with unoccupied binding sites of the binding protein-antibody complex bound to the solid support; observing the extent to which the indicator is present; correlating the extent to which the indicator is present with the amount of unknown analyte in the sample.

This invention further provides: a method for conducting a solid phase of a fluid sample with primary antibody to binding protein containing an unknown amount of analyte that binds binding protein, the method involving: immobilizing a sufficient amount of antibody to a binding protein, the antibody being of a specific or homologous species, the antibody being bound by an antibody against that species or a homologous species, on a solid support; treating the fluid mixture to free analyte from endogenous binding proteins; combining under binding conditions binding protein and free analyte to form a fluid mixture; applying the fluid mixture binding conditions to the solid support; applying an indicator to the solid phase under binding conditions to bind with unoccupied binding proteins; observing the extent to which the indicator is present on the solid support; and correlating the extent to which the indicator is present with the amount of unknown analyte in the sample.

The indicator may also be added to the fluid sample; this can be done by either adding the components at the same time or allowing the analyte and antibody to briefly incubate before the addition of the indicator. Binding conditions are further delineated in P. Tijssen, *Laboratory Techniques in Biochemistry*, Molecular Biology, Practice and Theory of Enzyme Immunoassay 123–145. (4th ed. 1987) (hereby incorporated by reference).

DETAILED DESCRIPTION OF THE INVENTION

Figure 1:
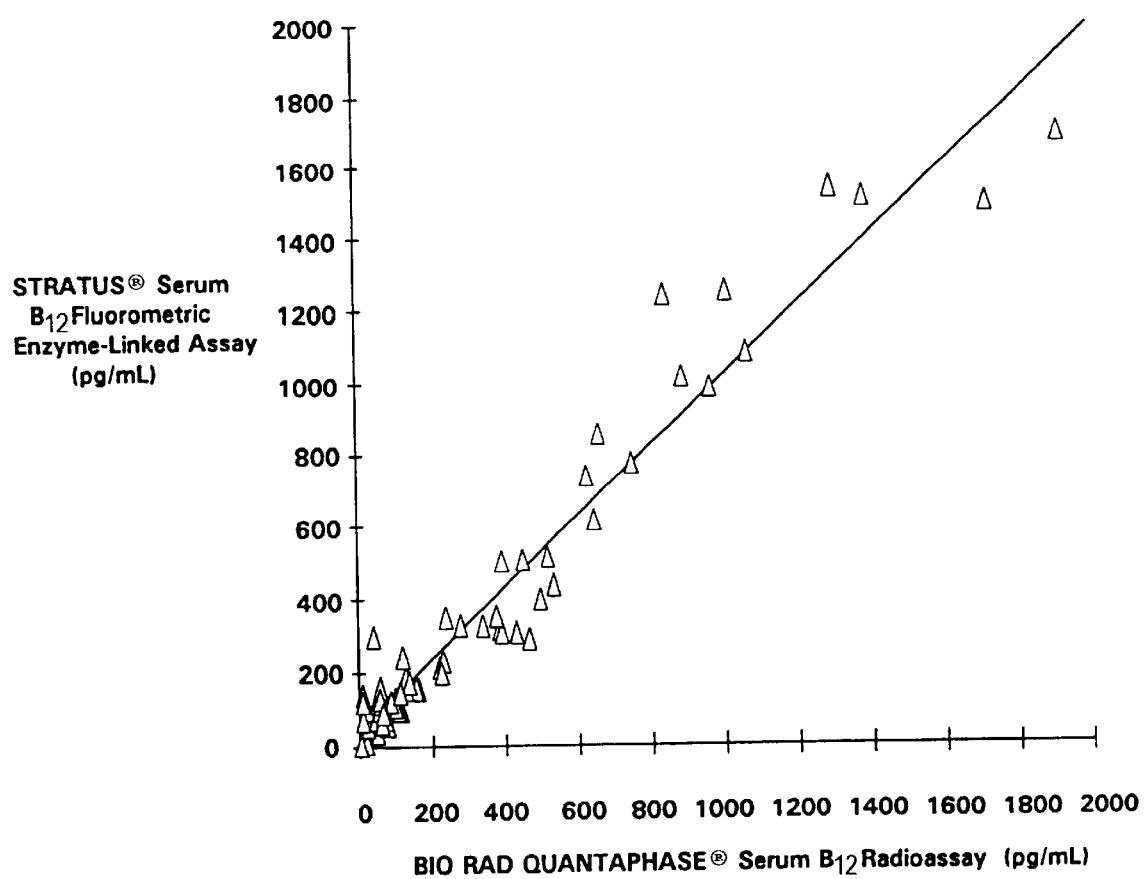
FIG. 1 shows a comparison of OUANTAPHASE (Bio Rad) B12 radioassay versus the presently disclosed B12 enzyme-linked assay.

The binding protein capture assay of the current invention involves a combination of specific binding proteins, and anti-binding protein antibodies. Antibodies to the binding proteins are herein referred to as primary antibodies. The anti-binding protein antibodies, described herein, recognize a site on the binding protein which is not required for analyte binding and, therefore, will bind either the binding protein or the binding protein analyte complex. The anti-binding protein antibodies function in the capture and orientation of the binding protein on solid surfaces.

More specifically, this invention provides an immunochemical reagent made of secondary antibodies. The immunochemical reagent may be made of anti-serum to a specific species. The anti-serum may be for example, goat anti-mouse, goat anti-rabbit, goat anti-sheep, sheep anti-goat, rabbit anti-goat, donkey anti-goat or more generally, a second species anti-first species. For purposes of this invention, anti-sera may be referred to herein as secondary antibody. The secondary antibody may be purified or unpurified. In certain embodiments, combinations of the various anti-sera may also be applied to the inert porous medium.

Because of the homology between certain strains of primary antibody, a secondary antibody developed against a species may also react with other closely related species. For example, goat anti-mouse will often react with primary antibody prepared from a rat. For purposes of this invention these species are referred to herein as homologous species.

The method of the present invention uses specific binding proteins and antibodies to these binding proteins to detect a physiologically active group of metabolites such an B12 or folate. The blood concentration of vitamin B12 and folate are useful in diagnosis of megloblastic anemia. In the context of these assays: analyte means a low molecular weight, weakly antigenic substance with high affinity for a binding protein. These analytes include but are not limited to: B12, folate, $T_4$, $T_3$, estradiol and testosterone. This assay is also useful with analytes or hormones that are associated with specific binding proteins. Additionally, enzymes could potentially be measured using this method. Other binding proteins useful in this invention include: thyroid binding globulin (TBG) Sex hormone Binding Globulin(s) (SHBG), enzymes. Additionally, it should be recognized that binding proteins themselves could be measured using this method and labelled analyte.

The solid support may be a glass fiber matrix "Tab", microsphere, or test tube etc. The solid support may include agents selectively retentive of an antibody such as protein A or protein G or of a modified antibody such as avidin conjugated to an antibody wherein the solid phase includes biotin or an antibody conjugated to lectin, wherein the solid phase includes a sugar. The solid support may include antibodies to a binding protein, binding protein and the binding protein antibodies of a specific species attached to the solid support by an antibody against that species or a homologous species; or binding protein bound to antibodies of a specific species attached to the solid support by an antibody against the species or a homologous species.

Preferably the solid support is coated with either goat anti-mouse IgG/Fc (Gam/Fc) or goat anti-mouse IgG/Fc, binding protein and monoclonal antibody to the binding protein. Additionally, enzymes could be potentially measured. In this method anti-enzyme antibodies (that bind distal to the active site) could be used to immobilize the enzymes on the solid phase and the amount of immobilized enzyme could be quantitated by the adding of a specific substrate.

The first step in the present assay involves denaturation of the sample to release analyte and destroy endogenous binding protein. The sample can be denatured to free the analyte by treatment with sodium hydroxide, boiling, chaotrophic agents (urea, potassium thiocyanate, guanidine, perchlorate), specific blockers (8-anilino-1-naphthalene-sulfonic acid or dihydro-testosterone) and by pH. Once the analyte is freed from endogenous binding protein the denatured sample is combined with a solution containing antibody against the nonbinding sequences of the exogenous binding protein and exogeneous binding protein. In this mixture analyte binding is improved since diffusion in liquid is the only rate limiting step.

This fluid mixture is added to a solid support consisting of a glass fiber paper having goat anti mouse IgG/Fc adsorbed to the tab. The binding protein antibody complexes are immobilized by the goat anti-mouse IgG/Fc antibody absorbed on to the solid support.

The term indicator in the context of this invention means a labeled conjugate. The conjugate is antibody or an analyte depending on the assay format. The label is a fluorescent, enzymatic, or colorometric or compound that is associated either directly or indirectly with the conjugate. The label may be comprised of an enzymatic compound that produces fluoresence upon contact with a substrate. The extent to which the indicator is present on the solid support can be correlated with the amount of unknown analyte in the sample.

EXAMPLE I

Assay for Vitamin B12

Preparation of glass fiber paper: A solution containing 3% (v/v) GAM/Fc and 50 mmol/L Tris, pH 8.0, was applied to GF/F glass-fiber paper and dried.

Preparation of enzyme labeled Conjugate: acid hydrolyzed B12 was linked to mammalian alkaline phosphatase via a succinimidyl ester linkage in 50 mmol/L Tris-maleate buffer, pH 7.2, containing 100 mmol/L galactose and 0.1% v/v ZONYL FSN a surfactant by Du Pont.

Preparation of assay Calibrators: Calibrators for this assay were prepared by addition of B12 to a 10 mmol/L phosphate buffer, pH 7.2, containing 5% (w/v) B12-free human serum albumin. Final concentrations for the calibrator set were 0, 100, 200, 400, 500 and 2000 pg B12/mL.

Preparation of Blocker: The Blocker for this assay is 50 mmol/L Borax, pH 9.2, containing 150 mmol/L sodium chloride and 1.2 µmol/L cobinamide dicyanide.

Preparation of extractant: The Extractant for this assay is 500 mmol/L sodium hydroxide containing 12% (v/v) ethanol and 1 mmol/L potassium cyanide.

Preparation of Neutralizer: 400 IU intrinsic factor was mixed with 6 mg mouse anti-intrinsic factor antibody in one liter of a 50 mmol/L Borax buffer, pH 9.2, containing 0.2% (w/v) B12-free human serum albumin and 0.5% (v/v) Brij-30.

Preparation of Substrate wash solution: The fluorogenic alkaline phosphatase substrate consists of 1 mmol/L 4-methylumbelliferyl phosphate in 1 mol/L, pH 9.0 diethanolamine buffer containing 3 mmol of magnesium acetate and 1 mmol of zinc sulfate per liter. 10 mmol/L Levamisole was added to inhibit residual serum alkaline phosphatase activity.

Assay procedure: Prior to assay, 60 µL of each calibrator, control and clinical specimen is diluted sequentially with 20 µL of blocker and 50 µL of Extractant. After a short incubation, 200 µL of Neutralizer is added to each diluted sample; B12 in the samples bind to the intrinsic factor/anti-intrinsic factor contained in the Neutralizer. Then, solid supports, glass fiber paper containing immobilized GAM/Fc, are introduced into the STRATUS® (Baxter Diagnostics, Inc.) Analyzer at a fixed loading station. An intermittent drive system pushes the top glass fiber paper on to a heated conveyor which moves the glass fiber paper to four different stations. At station #1 diluted sample is added to the glass fiber paper. Intrinsic factor/anti-instrinsic factor complexes (with or without bound B12) are allowed to bind to the immobilized GAM/Fc. After this reaction, the glass fiber paper is moved to station #2. Here, Conjugate is added to the glass fiber paper. The conjugate binds to the unoccupied intrinsic factor binding sites. During this reaction, the glass fiber paper is transported to station #3. When conjugate binding is complete, excess substrate wash is added to the glass fiber paper. Unbound conjugate and sample components are removed by radial elution and enzyme activity is initiated. See U.S. Pat. Nos. 4,517,288, 4,752,562, 4,774,174 and 4,786,606 (hereby incorporated by reference). The glass fiber paper is moved to station #4 where measurement occurs.

Results of a B12 Methods Comparison, QUANTAPHASE (Bio-Pad) versus the invention, are shown in FIG. 1.

EXAMPLE II

Assay for Folic Acid

Preparation of glass fiber papers: 26 mL GAM/Fc, 45 µg folate binding protein, 500 µg mouse anti-folate binding protein and 25 mL mouse serum were mixed in one liter of 50 mmol/L Tris, pH 8.0, containing 50 mmol/L sodium chloride and 0.1% (v/v) ZONYL FSN (DuPont)

Preparation of enzyme labeled Conjugate: folic acid linked to mammalian alkaline phosphatase via a succinimidyl ester linkage in (50 mmol/L Tris, pH 7.1, containing 0.3% (w/v) folate free bovine serum albumin 2 mmol/L MgCl and 0.2 mmol/zinc sulfate.

Preparation of assay Calibrators: Calibrators for this assay were prepared by addition of folic acid to a 50 mmol/L phosphate buffer, pH 7.2, containing 5.5% (w/v) folate-free bovine serum albumin, 150 mmol/L sodium chloride, 0.1% (v/v) Brij-35 and 0.35% (v/v) FSN. Final concentrations for the calibrator set were 0, 1, 2, 4, 8 and 15 ng folate/mL.

Preparation of Reductant: The Reductant for this assay is 1.0 mmol/L sodium phosphate, pH 6.5, containing 150 mmol/L sodium chloride, 2 mmol/L EDTA, 40 mmol/L Dithio-Threitol (DTT), and 275 mmol/L mannitol.

Preparation of Extractant: The extractant for this assay is 1.0 mol/L sodium hydroxide containing 25% (v/v) ethanol.

Preparation of Neutralizer: The Neutralizer for this assay is 50 mmol/L borax, pH 9.0.

Preparation of Substrate wash solution: The fluorogenic alkaline phosphatase substrate consists of 1 mmol/L 4-methylumbelliferyl phosphate in 1 mol/L, pH 9.0 diethanolamine buffer containing 3 mmol/L of magnesium acetate and 1 mmol/L of zinc sulfate per liter. 10 mmol/L Levamisole was added to inhibit residual serum alkaline phosphatase activity.

Assay procedure: Prior to assay, 50 $\mu$L of each calibrator, control and clinical specimen is diluted with 20 $\mu$L of Reductant. After a short incubation 20 $\mu$L of Extractant is added to the mixtures. After a second incubation, 200 $\mu$L of Neutralizer is added to each diluted sample. Then, glass fiber papers containing immobilized Goat anti-mouse/Fc/antifolate binding protein antibody/folate binding protein are introduced into the STRATUS® (Baxter Diagnostics, Inc.) Analyzer at a fixed loading station. An intermittent drive system pushes the top glass fiber paper onto a heated conveyor which moves the glass fiber paper to four different stations. At station #1 samples are added to glass fiber papers. Folate in the samples is allowed to bind to the immobilized folate binding protein. Next, the glass fiber paper is moved to station #2. Here, Conjugate is added to the glass fiber paper. The conjugate binds to the unoccupied folate binding protein binding sites. During this reaction, the glass fiber paper is transported to station #3. When Conjugate binding is complete, excess Substrate Wash is added to the glass fiber paper. Unbound Conjugate and sample components are removed by radial elution and enzyme activity is initiated. The glass fiber paper is moved to station #4 where measurement occurs.

Figure 2:
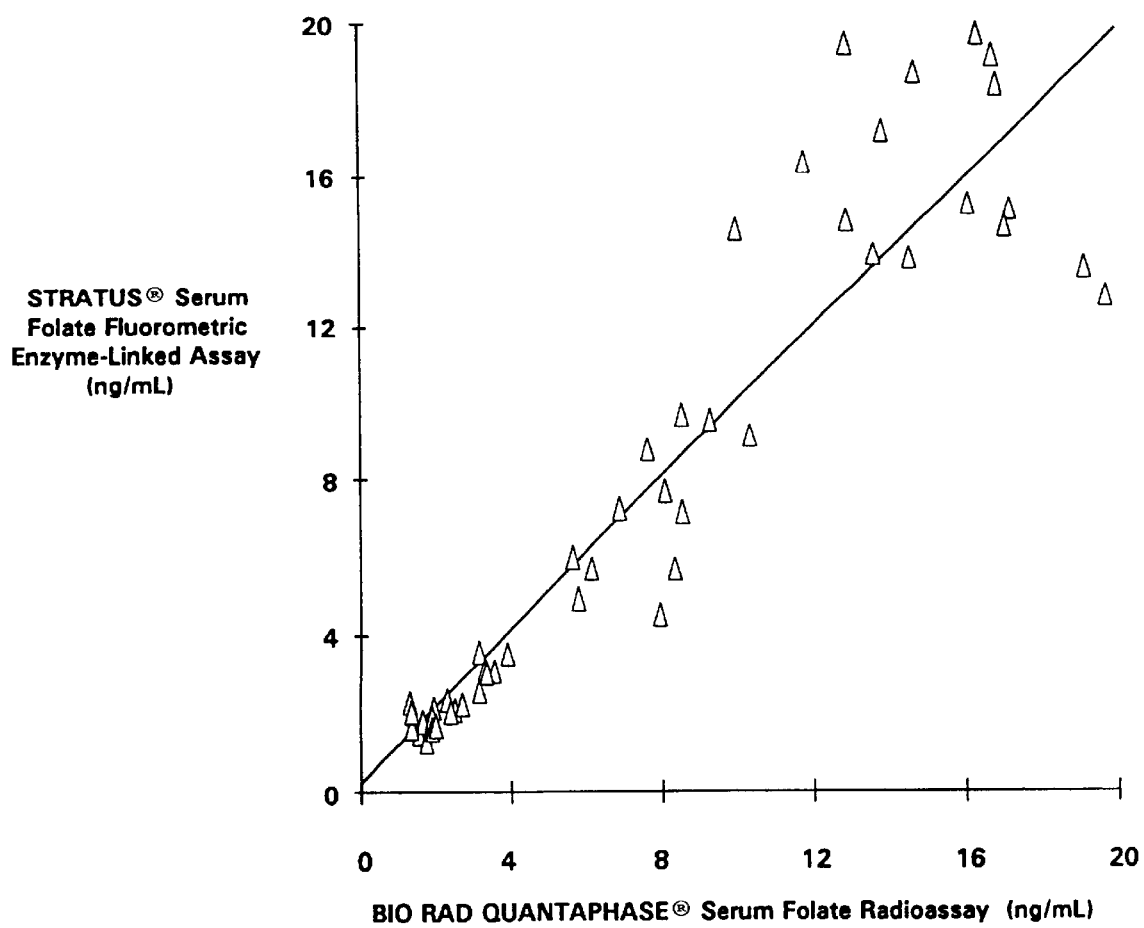
FIG. 2 shows a comparison of OUANTAPHASE (Bio Rad). Folate radioassay versus the presently disclosed Folate enzyme-linked assay.

The results of a Folate Methods Comparison, OUANTAPHASE (Bio-Rad) versus the invention, are shown in FIG. 2.

Although the invention has been described primarily in connection with special and preferred embodiments, it will be understood that it is capable of modification without departing from the scope of the invention. The following claims are intended to cover all variations, uses, or adaptations of the invention, following, in general, the principles thereof and including such departures from the present disclosure as come within known or customary practice in the field to which the invention pertains, or as are obvious to persons skilled in the field.

We claim:

1. A method to determine an amount of vitamin $B_{12}$ in a fluid sample, the fluid sample comprising at least some of the vitamin $B_{12}$ bound to endogenous intrinsic factor, the method comprising: treating the fluid sample to free any vitamin $B_{12}$ in the sample from endogenous intrinsic factor and to destroy the endogenous intrinsic factor's binding ability; combining the following with an amount of an immobilized primary antibody which specifically binds exogenous intrinsic factor: (a) an amount of exogenous intrinsic factor, (b) the treated fluid sample and (c) an amount of labelled vitamin $B_{12}$ whereby the immobilized primary antibody binds all of the exogenous intrinsic factor, and any vitamin $B_{12}$ in said sample and labeled vitamin $B_{12}$ compete for reaction with the exogenous intrinsic factor; measuring the amount of labeled vitamin $B_{12}$ bound to the primary antibody through the exogenous intrinsic factor; and using the measurement of the labeled vitamin $B_{12}$ to determine the amount of vitamin $B_{12}$ in the fluid sample.

2. A method to determine an amount of folate in a fluid sample, the fluid sample comprising at least some of the folate bound to endogenous folate binding protein, the method comprising: treating the fluid sample to free any folate in the sample from endogenous folate binding protein and to destroy the endogenous folate binding protein's binding ability; combining the following with an amount of an immobilized primary antibody which specifically binds folate binding protein: (a) an amount of exogenous folate binding protein, (b) the treated fluid sample and an amount of labelled folate whereby the immobilized primary antibody binds all of the exogenous folate binding protein, (c) and any folate in said sample and labeled folate compete for reaction with the exogenous folate binding protein; measuring the amount of labeled folate bound to the primary antibody through the exogenous folate binding protein; and using the measurement of the labeled folate to determine the amount of folate in the fluid sample.

3. A method to determine an amount of an analyte in a fluid sample, the fluid sample comprising at least some of the analyte bound to an endogenous specific binding protein, the method comprising: treating the fluid sample to free any of said analyte present in the sample from the endogenous specific binding protein and to destroy the endogenous specific binding protein's binding ability; combining the following with an amount of an immobilized primary antibody which reacts specifically with exogenous specific binding protein: (a) an amount of exogenous specific binding protein, (b) the treated fluid sample and (c) an amount of labelled analyte whereby the immobilized primary antibody binds all of the exogenous specific binding protein, and any of said analyte present in said sample and labeled analyte compete for reaction with the exogenous specific binding protein; measuring the amount of labeled analyte bound to the primary antibody through the exogenous specific binding protein; and using the measurement of the labeled analyte to determine the amount of analyte in the fluid sample.

\* \* \* \* \*